United States Patent
Hosabettu

(10) Patent No.: US 10,877,783 B2
(45) Date of Patent: Dec. 29, 2020

(54) SYSTEM AND METHOD FOR ALERTING A USER OF RISKS

(71) Applicant: WIPRO LIMITED, Bangalore (IN)

(72) Inventor: Raghavendra Hosabettu, Bangalore (IN)

(73) Assignee: Wipro Limited, Bangalore (IN)

( * ) Notice: Subject to any disclaimer, the term of this patent is extended or adjusted under 35 U.S.C. 154(b) by 307 days.

(21) Appl. No.: 15/667,663

(22) Filed: Aug. 3, 2017

(65) Prior Publication Data
US 2018/0365028 A1    Dec. 20, 2018

(30) Foreign Application Priority Data

Jun. 14, 2017 (IN) .............................. 201741020816

(51) Int. Cl.
*G06F 9/451* (2018.01)
*G08B 21/18* (2006.01)
(Continued)

(52) U.S. Cl.
CPC ............ *G06F 9/453* (2018.02); *A61B 5/1118* (2013.01); *A61B 5/746* (2013.01); *G08B 21/02* (2013.01); *G08B 21/182* (2013.01); *H04M 1/0264* (2013.01); *H04M 1/72538* (2013.01); *H04M 1/72569* (2013.01); *A61B 5/0002* (2013.01);
(Continued)

(58) Field of Classification Search
CPC ....... G06F 9/453; A61B 5/1118; A61B 5/746; A61B 2560/0242; A61B 5/0002; H04M 1/72569; H04M 1/72538; H04M 1/0264; H04M 2250/12; G08B 21/182;
(Continued)

(56) References Cited

U.S. PATENT DOCUMENTS 9,156,352 B2 * 10/2015 Kim .................... B60K 28/066
9,170,473 B1    10/2015 Li
(Continued)

FOREIGN PATENT DOCUMENTS

EP    2 981 061    2/2016

OTHER PUBLICATIONS

Author: Junhua Mao, Wei Xu, Yi Yang, Jiang Wang, Alan L. Yuille Title: Explain Images with Multimodal Recurrent Neural Networks Date: Oct. 2014 pp. 1-9 (Year: 2014).*

*Primary Examiner* — Ajay M Bhatia
*Assistant Examiner* — Phoebe X Pan
(74) *Attorney, Agent, or Firm* — Finnegan, Henderson, Farabow, Garrett & Dunner, LLP

(57) ABSTRACT

In one embodiment, a system, comprising a processor and a memory, for alerting a user, is disclosed. The processor receives one or more sensor data. The processor further determines one or more environmental factors, a current activity of the user, one or more motion data and one or more objects in proximity to the user based on the one or more sensor data. The processor further generates an initial degree of safety for each of the one or more environmental factors, the current activity of the user, the one or more motion data of the electronic device and the one or more objects in proximity to the user based on dynamically adaptive thresholds. The processor further generates an aggregate degree of safety based on the initial degree of safety and one or more pre-defined rules. The processor further alerts the user based on the aggregate degree of safety.

17 Claims, 3 Drawing Sheets

(51) Int. Cl.
  *G08B 21/02* (2006.01)
  *H04M 1/02* (2006.01)
  *H04M 1/725* (2006.01)
  *A61B 5/11* (2006.01)
  *A61B 5/00* (2006.01)
  *H04B 1/3827* (2015.01)
  *H04W 4/02* (2018.01)
  *H04W 4/90* (2018.01)
  *G08B 19/00* (2006.01)

(52) U.S. Cl.
  CPC ...... *A61B 2560/0242* (2013.01); *G08B 19/00* (2013.01); *H04B 1/3833* (2013.01); *H04M 2250/12* (2013.01); *H04W 4/027* (2013.01); *H04W 4/90* (2018.02)

(58) Field of Classification Search
  CPC ......... G08B 21/02; G08B 19/00; H04W 4/90; H04W 4/027; H04B 1/3833
  See application file for complete search history.

(56) References Cited

U.S. PATENT DOCUMENTS

| | | | | |
|---|---|---|---|---|
| 9,594,725 | B1* | 3/2017 | Cook | G06F 3/0482 |
| 9,990,846 | B1* | 6/2018 | Katz | G08G 1/056 |
| 10,013,773 | B1* | 7/2018 | Ogale | G06K 9/00791 |
| 10,506,411 | B1* | 12/2019 | Jacob | H04W 4/90 |
| 2007/0072553 | A1* | 3/2007 | Barbera | H04M 1/72577 455/67.11 |
| 2011/0309940 | A1* | 12/2011 | Hyde | G08B 3/10 340/600 |
| 2012/0011559 | A1* | 1/2012 | Miettinen | G06F 21/31 726/1 |
| 2012/0033860 | A1 | 2/2012 | Lung | |
| 2012/0185910 | A1* | 7/2012 | Miettinen | G06F 21/31 726/1 |
| 2013/0040619 | A1* | 2/2013 | Grube | H04W 4/90 455/414.1 |
| 2014/0111646 | A1 | 4/2014 | Hamilton, Sr. | |
| 2014/0359777 | A1* | 12/2014 | Lam | G06F 21/577 726/25 |
| 2016/0150070 | A1* | 5/2016 | Goren | H04W 4/029 455/404.2 |
| 2017/0213145 | A1* | 7/2017 | Pathak | G06N 7/005 |
| 2017/0309158 | A1* | 10/2017 | Qu | G08B 21/0453 |
| 2017/0310816 | A1* | 10/2017 | Rhyne | H04M 1/72577 |
| 2018/0075309 | A1* | 3/2018 | Sathyanarayana | G06K 9/00 |
| 2018/0267491 | A1* | 9/2018 | Gordon | G05B 9/02 |
| 2018/0329384 | A1* | 11/2018 | Georgeson | G05B 19/048 |
| 2019/0082044 | A1* | 3/2019 | Melendez | H04M 1/72569 |

* cited by examiner

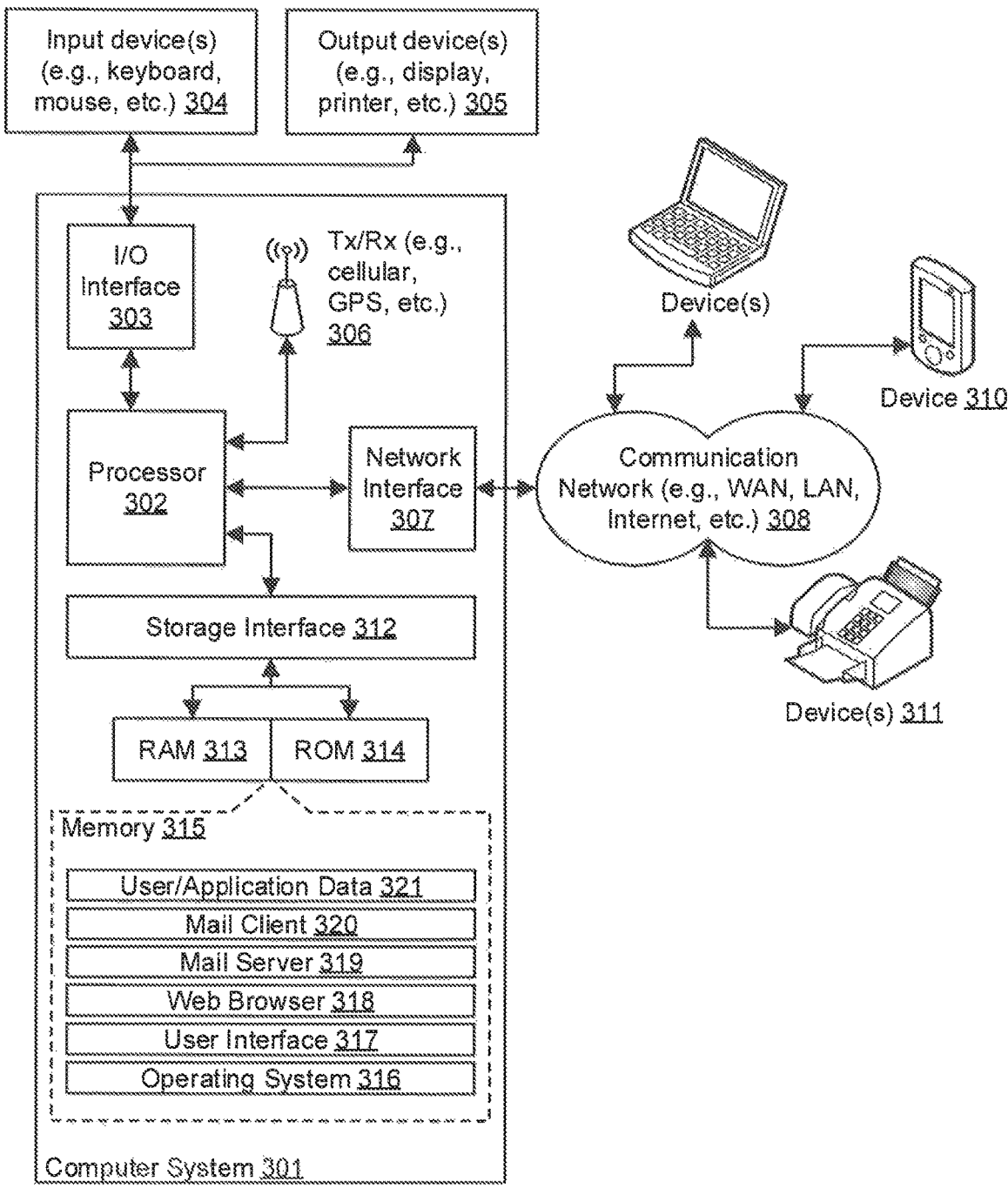
FIG. 3: Example Computer System

SYSTEM AND METHOD FOR ALERTING A USER OF RISKS

PRIORITY CLAIM

This U.S. patent application claims priority under 35 U.S.C. § 119 to Indian Patent Application No. 201741020816, filed Jun. 14, 2017. The aforementioned applications are incorporated herein by reference in theft entirety.

TECHNICAL FIELD

This disclosure relates generally to end user devices and more particularly to a system and method for alerting a user on the end user devices.

BACKGROUND

Electronic devices such as mobile phones, tablets, cameras have become an irreplaceable part of daily life of technologically sound people. Disadvantage of this engrossment into technological world is reduced awareness of users in public spaces, when the users are interacting with electronic devices. For instance, texting while crossing the road, taking a self-portrait photograph near a wild tiger, watching a video while climbing a hill etc. The lack of awareness of the user's surroundings, when they are interacting with the electronic devices, may be dangerous not only for the user, but also for the people in proximity to the user. In extreme situations, the lack of awareness may also lead to death.

One of the irresponsible interactions of the users with the electronic devices, that has become a major concern in recent years, is self-portrait photograph. Dangerous usage of self-portrait photographs, such as taking selfie at edge of a cliff, posing with a gun, taking selfie on a fast moving vehicle, taking selfie hi a funeral, public restroom etc., may lead to embarrassment, injuries or death. Hence, there arises a need for alerting the user of risks, while interacting with the electronic devices.

SUMMARY

In an embodiment, the present disclosure illustrates a method of alerting a user. The method comprising receiving one or more sensor data. The method further comprising determining one or more environmental factors, a current activity of the user, one or more motion data of the electronic device and one or more objects in proximity to the user based on the one or more sensor data. The method further comprising generating an initial degree of safety for each of the one or more environmental factors, the current activity of the user, the one or more motion data of the electronic device and the one or more objects in proximity to the user based on dynamically adaptive thresholds. The method further comprising generating an aggregate degree of safety based on the initial degree of safety and one or more pre-defined rules. The method further comprising alerting the user based on the aggregate degree of safety.

In another embodiment, the present disclosure illustrates a system for alerting a user. The system comprises a processor and a memory communicatively coupled to the processor. The memory stores processor instructions, which, on execution, causes the processor to receive one or more sensor data. The processor further determines one or more environmental factors, a current activity of the user, one or more motion data of the electronic device and one or more objects in proximity to the user based on the one or more sensor data. The processor further generates an initial degree of safety for each of the one or more environmental factors, the current activity of the user, the one or more motion data of the electronic device and the one or more objects in proximity to the user based on dynamically adaptive thresholds. The processor further generates an aggregate degree of safety based on the initial degree of safety and one or more pre-defined rules. The processor further alerts the user based on the aggregate degree of safety.

In yet another embodiment, a non-transitory computer readable storage medium is provided. The storage medium stores a program that, when executed by a computer, cause the computer to perform a method of alerting a user. The method comprises receiving one or more sensor data. The method further comprises determining one or more environmental factors, a current activity of the user, one or more motion data of the electronic device and one or more objects in proximity to the user based on the one or more sensor data. The method further comprises generating an initial degree of safety for each of the one or more environmental factors, the current activity of the user, the one or more motion data of the electronic device and the one or more objects in proximity to the user based on dynamically adaptive thresholds. The method further comprises generating an aggregate degree of safety based on the initial degree of safety and one or more pre-defined rules. The method further comprises alerting the user based on the aggregate degree of safety.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 3 is a block diagram of an exemplary computer system for implementing embodiments consistent with the present disclosure.

DETAILED DESCRIPTION

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

The present subject matter discloses a system and method for alerting a user of risks. The system and method may be implemented in a variety of computing systems.

Figure 1:
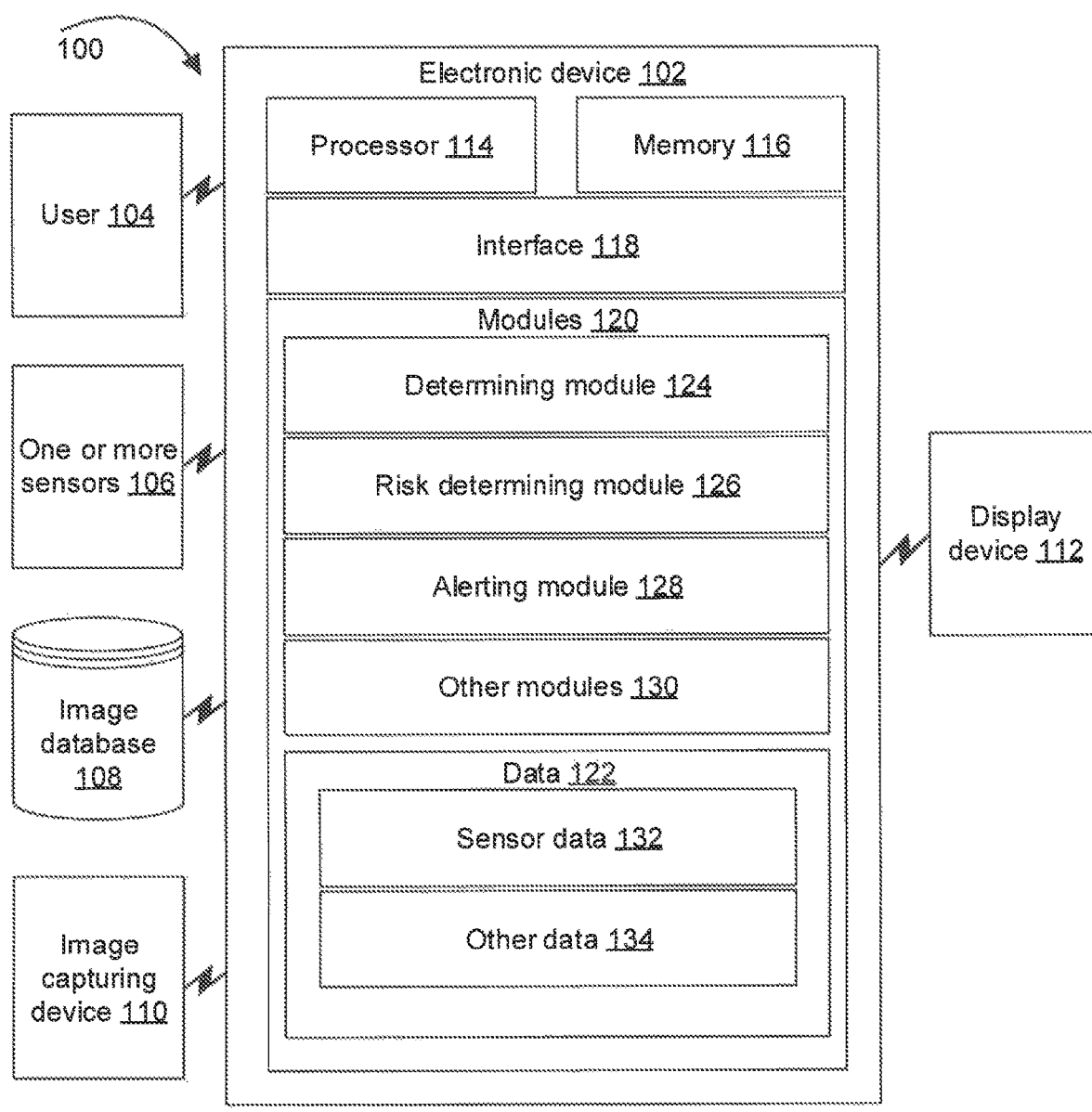
FIG. 1 illustrates an exemplary network implementation comprising an electronic device for alerting a user of risks, according to some embodiments of the present disclosure.
Figure 2:
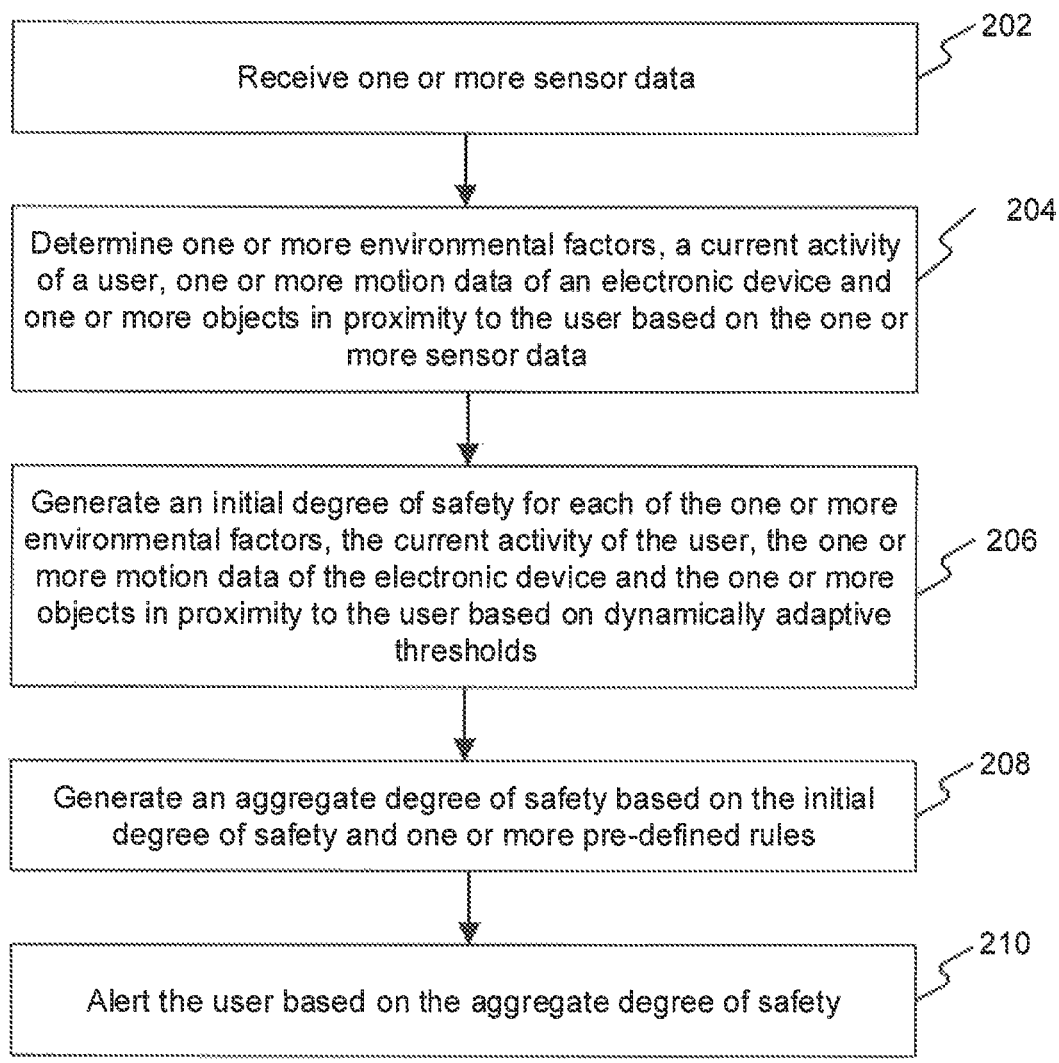
FIG. 2 is a flow diagram illustrating a method of alerting a user of risks in accordance with some embodiments of the present disclosure.

Working of the systems and methods for alerting a user of risks is described in conjunction with FIG. 1-3. It should be noted that the description and drawings merely illustrate the principles of the present subject matter. It will thus be appreciated that those skilled in the art will be able to devise various arrangements that, although not explicitly described or shown herein, embody the principles of the present subject matter and are included within its spirit and scope. Furthermore, all examples recited herein are principally intended expressly to be only for pedagogical purposes to aid the reader in understanding the principles of the present subject matter and are to be construed as being without limitation to such specifically recited examples and conditions. Moreover, all statements herein reciting principles, aspects, and embodiments of the present subject matter, as well as specific examples thereof, are intended to encompass equivalents thereof. While aspects of the systems and methods can be implemented in any number of different computing systems environments, and/or configurations, the embodiments are described in the context of the following exemplary system architecture(s).

FIG. 1 illustrates an exemplary network environment 100 comprising an electronic device 102, in accordance with some embodiments of the present disclosure. As shown in FIG. 1, the electronic device 102 is communicatively coupled to a user 104, one or more sensors 106, an image database 108, an image capturing device 110 and a display device 112. Although, the one or more sensors 106, the image database 108, the image capturing device 110 and the display device 112 is shown external to the electronic device 102 in FIG. 1, it may be noted that in one implementation, the one or more sensors 106, the image database 108, the image capturing device 110 and the display device 112 may be present within the electronic device 102.

The electronic device 102 may be communicatively coupled to the image database 108, the image capturing device 110 and the display device 112 through a network. The network may be a wireless network, wired network or a combination thereof. The network can be implemented as one of the different types of networks, such as intranet, local area network (LAN), wide area network (WAN), the Internet, and such. The network may either be a dedicated network or a shared network, which represents an association of the different types of networks that use a variety of protocols, for example, Hypertext Transfer Protocol (HTTP), Transmission Control Protocol/Internet Protocol (TCP/IP), Wireless Application Protocol (WAP), etc., to communicate with each other. Further, the network may include a variety of network devices, including routers, bridges, servers, computing devices, storage devices, etc.

As shown in FIG. 1, the electronic device 102 comprises a processor 114, a memory 116 coupled to the processor 114 and interface(s) 118. The processor 114 may be implemented as one or more microprocessors, microcomputers, microcontrollers, digital signal processors, central processing units, state machines, logic circuitries, and/or any devices that manipulate signals based on operational instructions. Among other capabilities, the processor 114 is configured to fetch and execute computer-readable instructions stored in the memory 116. The memory 116 can include any non-transitory computer-readable medium known in the art including, for example, volatile memory (e.g., RAM), and/or non-volatile memory (e.g., EPROM, flash memory, etc.).

The interface(s) 118 may include a variety of software and hardware interfaces, for example, a web interface, a graphical user interface, etc., allowing the electronic device 102 to interact with a user. Further, the interface(s) 118 may enable the electronic device 102 respectively to communicate with other computing devices. The interface(s) 118 can facilitate multiple communications within a wide variety of networks and protocol types, including wired networks, for example LAN, cable, etc., and wireless networks such as WLAN, cellular, or satellite. The interface(s) 118 may include one or more ports for connecting a number of devices to each other or to another server.

In one implementation, the electronic device 102 includes modules 120 and data 122. In one embodiment, the modules 120 and the data 122 may be stored within the memory 116. In one example, the modules 120, amongst other things, include routines, programs, objects, components, and data structures, which perform particular tasks or implement particular abstract datatypes.

In one implementation, the modules 120 include a determining module 124, a risk determining module 126 and an alerting module 128. In an example, the modules 120 may also comprise other modules 130. The other modules 130 may perform various miscellaneous functionalities of the electronic device 102. It will be appreciated that such aforementioned modules 120 may be represented as a single module or a combination of different modules.

In one example, the data 122 serves, among other things, as a repository for storing data fetched, processed, received and generated by one or more of the modules 120. In one implementation, the data 122 may include sensor data 132. In one embodiment, the data 122 may be stored in the memory 116 in the form of various data structures. In an example, the data 122 may also comprise other data 134 including temporary data and temporary files, generated by the modules 120 for performing the various functions of the electronic device 102.

In order to alert a user of risks, the electronic device 102 may receive one or more sensor data 132. Sensor data 132 may include location data, proximity data, luminance data, accelerometer data, gyroscope data, height from ground level, temperature, humidity and image data. In one embodiment, the location data may be determined using a Global Positioning System (GPS), the proximity data may be determined using proximity sensors such as inductive, capacitive, photoelectric, ultrasonic etc. In one embodiment, the luminance data may be identified using ambient light sensors, the accelerometer data may be extracted using accelerometers such as bulk micromachined capacitive, bulk micromachined piezoelectric resistive etc. and the gyroscope data may be extracted using gyroscopes such as ring laser and fiber optics gyroscopes, dynamically tuned gyroscopes etc. The height from ground level may be determined using pressure sensors such as gage, absolute or differential pressure sensors and the temperature may be determined using temperature sensors. The humidity may be determined using humidity sensors such as metal-paper coil type, hair tension hygrometers, psychrometer etc., and the image data may be determined using an image capturing device 110. The image data may comprise postures of the user 104, the number of people in the image etc.

After receiving the one or more sensor data 132, one or more environmental factors, a current activity of the user 104 (or user activity factor), one or more motion data of the electronic device 102 and one or more objects in proximity to the user 104 (or objects in proximity factor), may be determined from the one or more sensor data 132. The environmental factors may include height from ground level, posture of the user 104, location data, temperature, humidity or illumination. In one embodiment, the illumination may be extracted from the luminance data. In one embodiment, the environmental factors may be determined using ambient air temperature sensor, illuminance sensor, ambient air pressure sensor or ambient relative humidity sensor. The current activity of the user 104 may include running, walking, driving, biking or remaining still. In one embodiment, the current activity may be identified using accelerometer, temperature sensors, gyroscopes, pressure sensors and humidity sensors. In another embodiment, the current activity of the user 104 may be identified using an activity recognition Application Programming Interface (API).

The one or more motion data may include tilt, shake, rotation or swing. In one embodiment, motion data may be identified using geomagnetic field sensor, accelerometer or gyroscope sensor. In one embodiment, objects in proximity to the user 104 may include hills, valleys, vehicles, fire, water bodies, slippery surfaces, wild animals, safety notices or number of people. The objects in proximity to the user 104 may be determined using the image data from the image capturing device 110 and the proximity data from the proximity sensors.

In order to determine the objects in proximity to the user 104, initially, images captured by the image capturing device 110 is divided into several segments. Objects are then identified in each segment and then labelled. In one embodiment, the identification of objects is done using a multi-modal recurrent neural network (MRNN). The MRNN model consists of a deep recurrent neural network for sentences and a deep convolutional network for images. These two networks interact with each other in a multimodal layer. The MRNN is trained using several images that are extracted from the image database 108. The image database 108 comprise a plurality of historic images that were found to be either dangerous or safe, depending on the effect the user 104 had while interacting with the electronic device 102. The MRNN essentially enables conversion of an image into a sentence with context. This sentence with contexts may be used to identify the objects in proximity to the user 104. In one embodiment, natural language understanding techniques may be employed for comprehending safety notices that are available in the images.

After determining the environmental factors, the user activity factors, the motion data of the electronic device 102 and the objects in proximity factor, an initial degree of safety for each of the environmental factors, the user activity factors, the motion data and the objects in proximity factors, is generated. The initial degree of safety is indicative of scores assigned to each factor such as environmental factors, motion data etc. and may include safe, unsafe or care. If possibility of danger is above a first threshold, then the initial degree of safety may be unsafe. If the possibility of danger is above a second threshold (where the value of the second threshold is less than the value of the first threshold), but below the first threshold, then the initial degree of safety may be care. When the possibility of danger is below the second threshold, the initial degree of safety may be safe.

The first threshold and the second threshold may be dynamically adaptive thresholds. The thresholds may be dynamically adaptive based on the objects in proximity to the user 104. In one illustration, the image data and the proximity data may reveal that there is a forest in proximity to the user 104. The threshold for temperature is lowered since there is a risk of fire. This means that a lower degree of temperature may trigger the alert (unsafe) to the user 104 as compared to temperature threshold for a terrain without a forest in site. In another illustration, the terrain extracted from the image data may reveal that the area is a desert, then the threshold of the temperature needs to be increased, otherwise no user 104 will be able to message or take pictures in desert areas. In one embodiment, the user 104 may provide values for the first threshold and the second threshold via the interface 118.

In one illustration, the image data and the proximity data may reveal that even though the user 104 is inside a moving vehicle, the user 104 is not driving the vehicle. In the same illustration, the first and the second threshold for the corresponding current activity factor needs to be increased. This is because it is safe for the user 104 in the passenger seat to interact with the electronic device 102. In one illustration, the electronic device 102 may be in a moving train and the motion data may indicate constant shaking. This might not necessarily mean that care needs to be taken while interacting with the electronic device 102 in a train. Hence, the first threshold and the second threshold needs to be increased in this illustration.

After generating the initial degree of safety, the aggregate degree of safety is generated. The aggregate degree of safety may include safe, unsafe or care. The aggregate degree of safety is based on the initial degree of safety and one or more predefined rules. Initially, scores are assigned to each of the environmental factors, the user activity factors, the motion data and the objects in proximity factors. The scores are assigned based on the dynamically adaptive thresholds. The assigned scores are indicative of the initial degree of safety. After assigning the scores, maximum value of the assigned scores may be determined from each of the factors.

The maximum values of the factors along with the predefined rules may be used to generate the aggregate degree of safety. In one embodiment, the predefined rules may be that if the maximum value of user activity factor, objects in proximity factor and the environmental factor indicates that it is unsafe, then the aggregate degree of safety is unsafe. In one embodiment, if the maximum value of any two factors from the motion data, the objects in proximity factor, the environmental factor and the user activity is care, then the aggregate degree of safety is care. In one embodiment, if the maximum value of the motion data, alone, indicates that the motion data is unsafe, then the aggregate degree of safety is care.

TABLE 1

| Environmental Factors | | | | | | | |
|---|---|---|---|---|---|---|---|
| Height | Orientation | Location | Temperature | Humidity | Illumination | Max value | Output |
| 1 | 1 | 1 | 1 | 1 | 1 | 1 | Safe |
| 3 | 1 | 2 | 2 | 1 | 1 | 3 | unsafe |
| 2 | 1 | 1 | 1 | 1 | 1 | 2 | care |
| 2 | 2 | 2 | 2 | 2 | 2 | 2 | care |
| 3 | 3 | 3 | 3 | 3 | 3 | 3 | unsafe |

Table. 1 is an exemplary table that shows each of the environmental factors and the scores that are assigned to it, may indicate safe, '2' may indicate care and '3' may indicate unsafe. When the maximum value of the environmental factor indicates '3', that is unsafe, then the output corresponding to the environmental factor may be considered as unsafe. Similarly, when the maximum value of the environmental factor indicates '2', then the output corresponding to the environmental factor may be considered as care and when the maximum value of the environmental factor indicates '1', then the output corresponding to the environmental factor may be considered as safe. The output corresponding to the environmental factor may be used to generate the aggregate degree of safety.

TABLE 2

| Activities | Initial degree of safety |
|---|---|
| Remaining Still | Safe |
| Walking | Care |
| Running | Unsafe |
| In a vehicle | Unsafe |
| Biking | Unsafe |

Table. 2 is an exemplary table that shows each of the user activity factors and the corresponding initial degree of safety. This table is for representative purpose only. The initial degree of safety corresponding to each of the user activity factors may also depend on the dynamically adaptive thresholds. For instance, there might be situations where it is perfectly safe to interact with the electronic device 102, when the user 104 is in a vehicle and is not driving.

TABLE 3

| | | Motion data | | | |
|---|---|---|---|---|---|
| Tilt | Shake | Rotation | Swing | Max value | Output |
| 3 | 2 | 2 | 2 | 3 | Unsafe |
| 2 | 3 | 1 | 1 | 3 | Unsafe |
| 2 | 2 | 2 | 2 | 2 | Care |
| 1 | 1 | 1 | 1 | 1 | Safe |

Table. 3 is an exemplary table that indicates each of the motion data of the electronic device 102 and the scores that are assigned to them. If the maximum value of the motion data indicates '3', then the output corresponding to the motion data is considered as unsafe. When the maximum value of the motion data indicates '2', then the output corresponding to the motion data is considered as care. When the maximum value of the motion data indicates '1', then the output corresponding to the motion data is considered as safe. The output corresponding to the motion data may also be used to generate the aggregate degree of safety.

The output corresponding to the environmental factor, the user activity factor, the motion data and the objects in proximity factor may be used to determine the aggregate degree of safety. In one embodiment, the aggregate degree of safety may be determined from the output corresponding to the environmental factors, the user activity factors, the motion data and the objects in proximity factor, along with the predefined rules. In one embodiment, the predefined rules may be that if the maximum value of the user activity factor, the objects in proximity factor and the environmental factor indicates that it is unsafe, then the aggregate degree of safety is unsafe. In one embodiment, if the maximum value of any two factors from the motion data, the objects in proximity factor, the environmental factor and the user activity factor is care, then the aggregate degree of safety is care. In one embodiment, if the maximum value of the motion data, alone, indicates that the motion data is unsafe, then the aggregate degree of safety is care.

In another embodiment, the aggregate degree of safety may be generated by initially assigning weightages to the environmental factor, the user activity factor, the motion data and the objects in proximity factor. The weightages may depend on the objects in proximity to the user 104. After assigning weightages, the maximum value of the environmental factor, the user activity factor, the motion data and the objects in proximity factor and the assigned weightages may be used to determine an aggregate index.

$$\text{Aggregate index} = ENV*ENV_{Wt} + UA*UA_{Wt} + MD*MD_{Wt} + OBJ*OBJ_{Wt},$$

wherein the ENV indicates the maximum value of the environmental factor, UA indicates the maximum value of the user activity factor, MD indicates the maximum value of the motion data and the OBJ indicates the maximum value of the objects hi proximity factor. $ENV_{Wt}$ indicates the weightage assigned to the environmental factor, $UA_{Wt}$ indicates the weightage assigned to the user activity factor, $MD_{Wt}$ indicates the weightage assigned to the motion data and $OBJ_{Wt}$ indicates the weightage assigned to the objects in proximity factor.

In one illustration, when the aggregate index is above a particular threshold, then the aggregate degree of safety may still be unsafe, even if the maximum value of all the factors indicates care. In one embodiment, the particular threshold may be provided by the user 104 via the interface 118. In another embodiment, the particular threshold may be determined using an artificial neural network. The input for the artificial neural network may be the maximum value of factors associated with the historical data and the effect, associated with the historical data, on the user 104 interacting with the electronic device 102. For instance, the effect may be whether an accident had occurred or not.

After generating the aggregate degree of safety, the user 104 is alerted of potential danger while interacting with the electronic device 102. The alert is based on the aggregate degree of safety. In one embodiment, alerts, such as textual alert, graphical alert, vibration alert may be used. In another embodiment, features like calling, texting, capturing images etc. may be disabled after a predefined time interval from the time of alerting the user 104, depending on the severity of the aggregate degree of safety. This disabling feature ensures the safety of the user 104 even if the user 104 is still willing to take the risk of interacting with the electronic device 102, even after viewing the alert in the display device 112.

In one illustration, features maybe disabled when the aggregate degree of safety indicates unsafe. In the same illustration, when the aggregate degree of safety indicates safe or care, then the user 104 may be alerted using textual alert, graphical alert or vibration alert. The textual or graphical alert may be displayed using the display device 112.

In one illustration, the user 104 may be in a hilly area with a slippery surface. The image capturing device 110 of the electronic device 102 will automatically be turned on.

TABLE 4

Environmental Factors

| Height | orientation | location | temp | Humidity | illumination | Max | o/p |
|---|---|---|---|---|---|---|---|
| 1 | 1 | 1 | 2 | 1 | 1 | 2 | Care |

Table. 4 shows the scores that may be assigned to each of the environmental factors. The temperature might be low in hilly areas and hence the score assigned may be '2'. This makes the output of the environmental factor as care.

TABLE 5

Motion data

| Tilt | Shake | Rotation | Swing | Max | O/P |
|---|---|---|---|---|---|
| 1 | 2 | 2 | 2 | 2 | Care |

Table. 5 shows the scores that may be assigned to each of the motion data. When the user 104 is climbing a hilly area with slippery surfaces, then the electronic device might shake, rotate and swing. Hence the scores assigned to shake, rotation and swing may be '2', thus making the output of the motion data as care.

TABLE 6

User activity factor

| Remaining still | Walking | Running | In a vehicle | Biking | Max | O/P |
|---|---|---|---|---|---|---|
| 0 | 2 | 0 | 0 | 0 | 2 | Care |

Table. 6 shows the scores that may be assigned to each of the user activity factors. All sub-factors except walking will be assigned 0 since the user 104 is only climbing the hill by walking. The score that is assigned to waking may be 2, which makes the output of the user activity factor, as care,

TABLE 7

Objects in proximity factor

| Hills | Valleys | Slippery Surface | Safety notices | No. of people | Wild animals | Max | O/P |
|---|---|---|---|---|---|---|---|
| 3 | 3 | 3 | 0 | 1 | 0 | 3 | Unsafe |

Table. 7 shows the scores that may be assigned to each of the objects in proximity factors. In the illustration, the images captured by the image capturing device 110 may not reveal the presence of wild animals or safety notices. Hence the scores assigned to the wild animals and safety notices may be 0. Presence of hills, valleys, slippery surfaces may be identified from the images and the scores assigned to them may be '3'. This makes the output of the objects in proximity factor as unsafe.

In the same illustration, the outputs associated with the factors are analyzed to determine the aggregate degree of safety. The outputs associated with the environmental factor, the motion data, the user activity factor is care. The output associated with the objects in proximity factor is unsafe. When we apply the predefined rules, the aggregate degree of safety becomes unsafe since one of the outputs are unsafe.

FIG. 2 is a flow diagram illustrating a method of alerting a user 104 of risks. With reference to FIG. 2, one or more sensor data 132 may be received at step 202. Sensor data 132 may include location data, proximity data, luminance data, accelerometer data, gyroscope data, height from ground level, temperature, humidity and image data. In one embodiment, the location data may be determined using a Global Positioning System (GPS), the proximity data may be determined using proximity sensors such as inductive, capacitive, photoelectric, ultrasonic etc. In one embodiment, the luminance data may be identified using ambient light sensors, the accelerometer data may be extracted using accelerometers such as bulk micromachined capacitive, bulk micromachined piezoelectric resistive etc. and the gyroscope data may be extracted using gyroscopes such as ring laser and fiber optics gyroscopes, dynamically tuned gyroscopes etc. The height from ground level may be determined using pressure sensors such as gage, absolute or differential pressure sensors and the temperature may be determined using temperature sensors. The humidity may be determined using humidity sensors such as metal-paper coil type, hair tension hygrometers, psychrometer etc., and the image data may be determined using an image capturing device 110. The image data may comprise postures of the user 104, the number of people in the image etc.

After receiving the one or more sensor data 132, one or more environmental factors, a current activity of the user 104 (or user activity factor), one or more motion data of the electronic device 102 and one or more objects in proximity to the user 104 (or objects in proximity factor), may be determined from the one or more sensor data 132, at step 204. The environmental factors may include height from ground level, posture of the user 104, location data, temperature, humidity or illumination. In one embodiment, the illumination may be extracted from the luminance data. In one embodiment, the environmental factors may be determined using ambient air temperature sensor, illuminance sensor, ambient air pressure sensor or ambient relative humidity sensor. The current activity of the user 104 may include running, walking, driving, biking or remaining still. In one embodiment, the current activity may be identified using accelerometer, temperature sensors, gyroscopes, pressure sensors and humidity sensors. In another embodiment, the current activity of the user 104 may be identified using an activity recognition Application Programming Interface (API).

The one or more motion data may include tilt, shake, rotation or swing. In one embodiment, motion data may be identified using geomagnetic field sensor, accelerometer or gyroscope sensor. In one embodiment, objects in proximity to the user 104 may include hills, valleys, vehicles, fire, water bodies, slippery surfaces, wild animals, safety notices or number of people. The objects in proximity to the user 104 may be determined using the image data from the image capturing device 110 and the proximity data from the proximity sensors.

In order to determine the objects in proximity to the user 104, initially, images captured by the image capturing device 110 is divided into several segments. Objects are then identified in each segment and then labelled. In one embodiment, the identification of objects is done using a multimodal recurrent neural network (MRNN). The MRNN model consists of a deep recurrent neural network for sentences and a deep convolutional network for images. These two networks interact with each other in a multimodal layer. The MRNN is trained using several images that are extracted from the image database 108. The image database 108 comprises a plurality of historic images that were found to be either dangerous or safe, depending on the effect on the user 104 while interacting with the electronic device 102. The MRNN essentially enables conversion of an image into a sentence with contexts. This sentence with contexts may be used to identify the objects in proximity to the user 104. In one embodiment, natural language understanding techniques may be employed for comprehending safety notices that are available in images.

After determining the environmental factors, the user activity factor, the motion data of the electronic device 102 and the objects in proximity factor, an initial degree of safety for each of the environmental factors, the user activity factor, the motion data and the objects in proximity factor, is generated, at step 206. The initial degree of safety is indicative of scores assigned to each factor such as environmental factors, motion data etc. and may include safe, unsafe or care. If possibility of danger is above a first threshold, then the initial degree of safety may be unsafe. If the possibility of danger is above a second threshold (where the value of the second threshold is less than the value of the first threshold), but below the first threshold, then the initial degree of safety may be care. When the possibility of danger is below the second threshold, the initial degree of safety may be safe.

The first threshold and the second threshold may be dynamically adaptive thresholds. The thresholds may be dynamically adaptive based on the objects in proximity to the user 104. In one illustration, the image data and the proximity data may reveal that there is a forest in proximity to the user 104. The threshold for temperature is lowered since there is a risk of fire. This means that a lower degree of temperature may trigger the alert (unsafe) to the user 104 as compared to temperature threshold for a terrain without a forest in site. In another illustration, the terrain extracted from the image data may reveal that the area is a desert, then the threshold of the temperature needs to be increased, otherwise no user 104 will ever be able to message or take pictures in desert areas. In one embodiment, the user 104 may provide values for the first threshold and the second threshold via the interface 118.

After generating the initial degree of safety, the aggregate degree of safety is generated, at step 208. The aggregate degree of safety may include safe, unsafe or care. The aggregate degree of safety is based on the initial degree of safety and one or more pre-defined rules. Initially, scores are assigned to each of the environmental factors, the user activity factors, the motion data and the objects in proximity factors. The scores are assigned based on the dynamically adaptive thresholds. The assigned scores are indicative of the initial degree of safety. After assigning the scores, maximum value of the assigned scores may be determined from each of the factors.

The maximum values of the factors along with the pre-defined rules may be used to generate the aggregate degree of safety. In one embodiment, the predefined rules may be that if the maximum value of user activity factor, objects in proximity factor and the environmental factor indicates that it is unsafe, then the aggregate degree of safety is unsafe. In one embodiment, if the maximum value of any two factors from the motion data, the objects in proximity factor, the environmental factor and the user activity factor is care, then the aggregate degree of safety is care. In one embodiment, if the maximum value of the motion data, alone, indicates that the motion data is unsafe, then the aggregate degree of safety is care.

The output corresponding to the environmental factor, the user activity factor, the motion data and the objects in proximity factor and the predefined rules may be used to determine the aggregate degree of safety. In one embodiment, the aggregate degree of safety may be determined from the output corresponding to the environmental factors, the user activity factors, the motion data and the objects in proximity factor, along with the predefined rules.

In another embodiment, the aggregate degree of safety may be generated by initially assigning weightages to the environmental factor, the user activity factor, the motion data and the objects in proximity factor. The weightages may depend on the objects in proximity to the user 104. After assigning weightages, the maximum value of the environmental factor, the user activity factor, the motion data and the objects in proximity factor and the assigned weightages may be used to determine an aggregate index.

$$\text{Aggregate index} = ENV*ENV_{Wt} + UA*UA_{Wt} + MD*MD_{Wt} + OBJ*OBJ_{Wt}$$

wherein the ENV indicates the maximum value of the environmental factor, UA indicates the maximum value of the user activity factor, MD indicates the maximum value of the motion data and the OBJ indicates the maximum value of the objects in proximity factor. $ENV_{Wt}$ indicates the weightage assigned to the environmental factor, $UA_{Wt}$ indicates the weightage assigned to the user activity factor, $MD_{Wt}$ indicates the weightage assigned to the motion data and $OBJ_{Wt}$ indicates the weightage assigned to the objects in proximity factor.

In one illustration, when the aggregate index is above a particular threshold, then the aggregate degree of safety may still be unsafe, even if the maximum value of all the factors indicates care. In one embodiment, the particular threshold may be provided by the user 104 via the interface 118. In another embodiment, the particular threshold may be determined using an artificial neural network. The input for the artificial neural network may be the maximum value of factors associated with the historical data and the effect, associated with the historical data, on the user 104 interacting with the electronic device 102. For instance, the effect may be whether an accident had occurred or not.

After generating the aggregate degree of safety, the user 104 is alerted of potential danger while interacting with the electronic device 102, at step 210. The alert is based on the aggregate degree of safety. In one embodiment, alerts, such as textual alert, graphical alert, vibration alert may be used. In another embodiment, features like calling, texting, capturing images etc. may be disabled after a predefined time interval from the time of alerting, depending on the severity of the aggregate degree of safety. This disabling feature ensures the safety of the user 104 even if the user 104 is still willing to take the risk of interacting with the electronic device 102, even after viewing the alert in the display device 112.

Computer System

PG. 3 is a block diagram of an exemplary computer system for implementing embodiments consistent with the present disclosure. Variations of computer system 301 may be used for implementing the electronic device. Computer system 301 may comprise a central processing unit ("CPU" or "processor") 302. Processor 302 may comprise at least one data processor for executing program components for executing user- or system-generated requests. A user may include a person, a person using a device such as such as those included in this disclosure, or such a device itself. The processor may include specialized processing units such as integrated system (bus) controllers, memory management control units, floating point units, graphics processing units, digital signal processing units, etc. The processor may include a microprocessor, such as AMD Athlon, Duron or Opteron, ARM's application, embedded or secure processors, IBM PowerPC, Intel's Core, Itanium, Xeon, Celeron or other line of processors, etc. The processor 302 may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), etc.

Processor 302 may be disposed in communication with one or more input/output (I/O) devices via I/O interface 303. The I/O interface 303 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 303, the computer system 301 may communicate with one or more I/O devices. For example, the input device 304 may be an antenna, keyboard, mouse, joystick, (infrared) remote control, camera, card reader, fax machine, dangle, biometric reader, microphone, touch screen, touchpad, trackball, sensor (e.g., accelerometer, light sensor, GPS, gyroscope, proximity sensor, or the like), stylus, scanner, storage device, transceiver, video device/source, visors, etc. Output device 305 may be a printer, fax machine, video display (e.g., cathode ray tube (CRT), liquid crystal display (LCD), light-emitting diode (LED), plasma, or the like), audio speaker, etc. In some embodiments, a transceiver 306 may be disposed in connection with the processor 302. The transceiver may facilitate various types of wireless transmission or reception. For example, the transceiver may include an antenna operatively connected to a transceiver chip (e.g., Texas Instruments WiLink WL1283, Broadcom BCM4750IUB8, Infineon Technologies X-Gold 618-PMB9800, or the like), providing IEEE 802.11a/b/g/n, Bluetooth, FM, global positioning system (GPS), 2G/3G HSDPA/HSUPA communications, etc.

In some embodiments, the processor 302 may be disposed in communication with a communication network 308 via a network interface 307. The network interface 307 may communicate with the communication network 308. The network interface may employ connection protocols including, without limitation, direct connect, Ethernet (e.g., twisted pair 10/100/1000 Base T), transmission control protocol/internet protocol (TCP/IP), token ring, IEEE 802.11a/big/nix, etc. The communication network 308 may include, without limitation, a direct interconnection, local area network (LAN), wide area network (WAN), wireless network (e.g., using Wireless Application Protocol), the Internet, etc. Using the network interface 307 and the communication network 308, the computer system 301 may communicate with devices 310, 311, and 312. These devices may include, without limitation, personal computer(s), server(s), fax machines, printers, scanners, various mobile devices such as cellular telephones, smartphones (e.g., Apple iPhone, Blackberry, Android-based phones, etc.), tablet computers, eBook readers (Amazon Kindle, Nook, etc.), laptop computers, notebooks, gaming consoles (Microsoft Xbox, Nintendo DS, Sony PlayStation, etc.), or the like. In some embodiments, the computer system 301 may itself embody one or more of these devices.

In some embodiments, the processor 302 may be disposed in communication with one or more memory devices 315 (e.g., RAM 313, ROM 314, etc.) via a storage interface 312. The storage interface may connect to memory devices 315 including, without limitation, memory drives, removable disc drives, etc., employing connection protocols such as serial advanced technology attachment (SATA), integrated drive electronics (IDE), IEEE-1394, universal serial bus (USB), fiber channel, small computer systems interface (SCSI), etc. The memory drives may further include a drum, magnetic disc drive, magneto-optical drive, optical drive, redundant array of independent discs (RAID), solid-state memory devices, solid-state drives, etc.

The memory devices 315 may store a collection of program or database components, including, without limitation, an operating system 316, user interface application 317, web browser 318, mail server 319, mail client 320, user/application data 321 (e.g., any data variables or data records discussed in this disclosure), etc. The operating system 316 may facilitate resource management and operation of the computer system 301. Examples of operating systems include, without limitation, Apple Macintosh OS X, Unix, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple iOS Google Android, Blackberry OS, or the like. User interface 317 may facilitate display, execution, interaction, manipulation, or operation of program components through textual or graphical facilities. For example, user interfaces may provide computer interaction interface elements on a display system operatively connected to the computer system 301, such as cursors, icons, check boxes, menus, scrollers, windows, widgets, etc. Graphical user interfaces (GUIs) may be employed, including, without limitation, Apple Macintosh operating systems' Aqua, IBM OS/2, Microsoft Windows (e.g., Aero, Metro, etc.), Unix X-Windows, web interface libraries (e.g., ActiveX, Java, Javascript, AJAX, HTML, Adobe Flash, etc.), or the like.

In some embodiments, the computer system 301 may implement a web browser 318 stored program component. The web browser may be a hypertext viewing application, such as Microsoft Internet Explorer, Google Chrome, Mozilla Firefox, Apple Safari, etc. Secure web browsing may be provided using HTTPS (secure hypertext transport protocol), secure sockets layer (SSL), Transport Layer Security (TLS), etc. Web browsers may utilize facilities such as AJAX, DHTML, Adobe Flash, JavaScript, Java, application programming interfaces (APIs), etc. In some embodiments, the computer system 301 may implement a mail server 319 stored program component. The mail server may be an Internet mail server such as Microsoft Exchange, or the like. The mail server may utilize facilities such as ASP, ActiveX, ANSI C++/C #, Microsoft .NET, CGI scripts, Java, JavaScript, PERL, PHP, Python, WebObjects, etc. The mail server may utilize communication protocols such as internet message access protocol (IMAP), messaging application programming interface (MAPI), Microsoft Exchange, post office protocol (POP), simple mail transfer protocol (SMTP), or the like. In some embodiments, the computer system 301 may implement a mail client 320 stored program component. The mail client may be a mail viewing application, such as Apple Mail, Microsoft Entourage, Microsoft Outlook, Mozilla Thunderbird, etc.

In some embodiments, computer system 301 may More user/application data 321, such as the data, variables, records, etc. as described in this disclosure. Such databases may be implemented as fault-tolerant, relational, scalable, secure databases such as Oracle or Sybase. Alternatively, such databases may be implemented using standardized data structures, such as an array, hash, linked list, struct, structured text file (e.g., XML), table, or as object-oriented databases (e.g., using ObjectStore, Poet, Zope, etc.), Such databases may be consolidated or distributed, sometimes among the various computer systems discussed above in this disclosure. It is to be understood that the structure and operation of the any computer or database component may be combined, consolidated, or distributed in any working combination.

The specification has described application title. The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A method of alerting a user of a mobile phone, the method comprising:
   receiving, by the mobile phone, one or more sensor data when the user interacting with at least one feature of the mobile phone, wherein the at least one feature comprises a calling feature, a texting feature, and an image capturing feature;
   identifying, by the mobile phone, one or more objects in proximity to the user based on image data from an image capturing device in the mobile phone, using a multi-modal recurrent neural network (MRNN) model that comprises a deep recurrent neural network for sentences and a deep convolutional network for images,
      wherein using the MRNN model comprises converting the image data into a sentence with contexts for identifying the one or more objects in proximity to the user;
   determining, by the mobile phone, one or more environmental factors, a current activity of the user, and motion data of the mobile phone-based on the one or more sensor data;
   determining, by the mobile phone, threshold values for the following factors: the one or more environmental factors, the current activity of the user, and the motion data of the mobile phone, using an artificial neural network based on:
      (i) the one or more objects in proximity to the user, and
      (ii) maximum value of factors associated with historical data, and an associated effect pertaining to the historical data, wherein the associated effect indicates an accident that happened to the user while interacting with mobile phone;
   generating, by the mobile phone, an initial degree of safety using the following factors: of the one or more environmental factors, the current activity of the user, and the motion data of the mobile phone based on the threshold values;
   generating, by the mobile phone, an aggregate degree of safety based on the initial degree of safety and one or more pre-defined rules; and
   alerting, by the mobile phone, the user based on severity of the aggregate degree of safety.

2. The method as claimed in claim 1, wherein the user is alerted of one or more potentially dangerous situations to operate the mobile phone.

3. The method as claimed in claim 1, wherein the one or more environmental factors comprises at least one of height from ground level, posture of the user, location, temperature, humidity or illumination.

4. The method as claimed in claim 1, wherein the current activity of the user comprises at least one of running, walking, driving, biking or remaining still.

5. The method as claimed in claim 1, wherein the motion data of the mobile phone comprises at least one of tilt, shake, rotation or swing.

6. The method as claimed in claim 1, wherein the one or more objects in proximity to the user comprises at least one of hills, valleys, vehicles, fire, water bodies, slippery surfaces, wild animals, safety notices or number of people.

7. The method as claimed in claim 1, wherein the initial degree of safety and the aggregate degree of safety comprises at least one of safe, unsafe or care.

8. The method as claimed in claim 1, further comprising disabling the at least one feature of the mobile phone after a predefined time interval from the time of alerting the user.

9. A system for alerting a user, the system comprising:
   a processor;
   a memory communicatively coupled to the processor, wherein the memory stores the processor-executable instructions, which, on execution, causes the processor to:
   receive one or more sensor data when the user interacting with at least one feature of the mobile phone, wherein the at least one feature comprises a calling feature, a texting feature, and an image capturing feature;
   identify one or more objects in proximity to the user based on image data from an image capturing device in the mobile phone, using a multi-modal recurrent neural network (MRNN) model that comprises a deep recurrent neural network for sentences and a deep convolutional network for images, wherein using the MRNN model comprises converting the image data into a sentence with contexts for identifying the one or more objects in proximity to the user;

determine one or more environmental factors, a current activity of the user, and one or more motion data of the mobile phone based on the one or more sensor data;

determine threshold values for the following factors: the one or more environmental factors, the current activity of the user, and the motion data of the mobile phone, using an artificial neural network based on
(i) the one or more objects in proximity to the user, and
(ii) maximum value of factors associated with historical data and an associated effect pertaining to the historical data, wherein the associated effect indicates an accident that happened to the user while interacting with mobile phone;

generate an initial degree of safety using the following factors: the one or more environmental factors, the current activity of the user, and the motion data of the mobile phone based on the threshold values;

generate an aggregate degree of safety based on the initial degree of safety and one or more pre-defined rules; and alert the user based on severity of the aggregate degree of safety.

10. The system as claimed in claim 9, wherein the user is alerted of one or more potentially dangerous situations to operate the mobile phone.

11. The system as claimed in claim 9, wherein the one or more environmental factors comprises at least one of height from ground level, posture of the user, location, temperature, humidity or illumination.

12. The system as claimed in claim 9, wherein the current activity of the user comprises at least one of running, walking, driving, biking or remaining still.

13. The system as claimed in claim 9, wherein the motion data of the mobile phone comprises at least one of tilt, shake, rotation or swing.

14. The system as claimed in claim 9, wherein the one or more objects in proximity to the user comprises at least one of hills, valleys, vehicles, fire, water bodies, slippery surfaces, wild animals, safety notices or number of people.

15. The system as claimed in claim 9, wherein the initial degree of safety and the aggregate degree of safety comprises at least one of safe, unsafe or care.

16. The system as claimed in claim 9, wherein the processor is further configured to disable the at least one feature of the mobile phone after a predefined time interval from the time of alerting the user.

17. A non-transitory computer readable storage medium storing a program that, when executed by a computer, cause the computer to perform a method of alerting a user of the mobile phone, the method comprising:

receiving one or more sensor data when the user interacting with at least one feature of the mobile phone, wherein the at least one feature comprises a calling feature, a texting feature, and an image capturing feature;

identifying one or more objects in proximity to the user based on image data from an image capturing device in the mobile phone, using a multi-modal recurrent neural network (MRNN) model that comprises a deep recurrent neural network for sentences and a deep convolutional network for images,
wherein using the MRNN model comprises converting the image data into a sentence with contexts for identifying the one or more objects in proximity to the user;

determining one or more environmental factors, a current activity of the user, and one or mom motion data of the mobile phone based on the one or more sensor data;

determining, by the mobile phone, threshold values for the following factors: the one or more environmental factors, the current activity of the user, and the motion data of the mobile phone, using an artificial neural network based on:
(i) the one or more objects in proximity to the user, and
(ii) maximum value of factors associated with historical data and an associated effect pertaining to the historical data, wherein the associated effect indicates an accident that happened to the user while interacting with mobile phone;

generating an initial degree of safety using the following factors: the one or more environmental factors, the current activity of the user, and the motion data of the mobile phone based on the threshold values;

generating an aggregate degree of safety based on the initial degree of safety and one or more pre-defined rules; and alerting the user based on severity of the aggregate degree of safety.

* * * * *